United States Patent [19]

Lares et al.

[11] 4,431,412
[45] Feb. 14, 1984

[54] DENTAL HANDPIECE

[75] Inventors: Joseph P. Lares, Redwood City; Albert J. Lares, San Carlos, both of Calif.

[73] Assignee: Lares Mfg. Co., Inc., San Carlos, Calif.

[21] Appl. No.: 248,866

[22] Filed: Mar. 30, 1981

[51] Int. Cl.³ .......................... A61C 1/00; A61C 1/08
[52] U.S. Cl. ...................................... 433/29; 433/126
[58] Field of Search ................. 433/126, 29, 32, 82; 285/136; 350/96.22; 362/32

[56] References Cited

U.S. PATENT DOCUMENTS

| 3,397,457 | 8/1968 | Gosselin | 433/29 |
| 3,893,242 | 7/1975 | Lieb et al. | 433/29 |
| 3,897,134 | 7/1975 | Scrivo et al. | 433/29 |
| 4,080,737 | 3/1978 | Fleer | 433/126 |
| 4,217,101 | 8/1980 | Loge | 433/126 |
| 4,260,382 | 4/1981 | Thomson | 433/29 |

Primary Examiner—John J. Wilson
Attorney, Agent, or Firm—Lothrop & West

[57] ABSTRACT

A dental handpiece has two sleeves rotatable relative to each other about a longitudinal axis. A chuck for a burr is driven by a gas turbine mounted in one of the sleeves. Air to drive the turbine is conducted through both sleeves by passages having a joint swivelling about the axis. Similarly, light, cleansing air and water are carried to the turbine vicinity and through swivel connections so that relative rotation of the handpiece sleeves can always be accomplished without interrupting any of the flows between the two sleeves.

2 Claims, 7 Drawing Figures

U.S. Patent  Feb. 14, 1984  Sheet 1 of 2  4,431,412
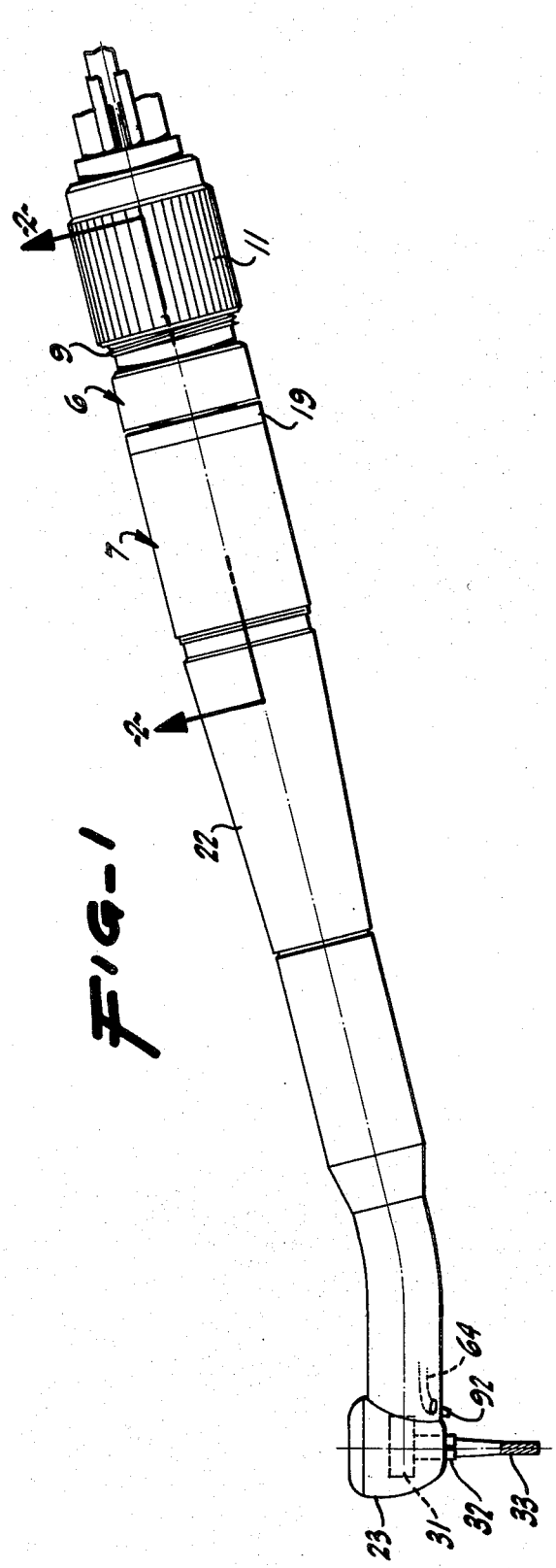
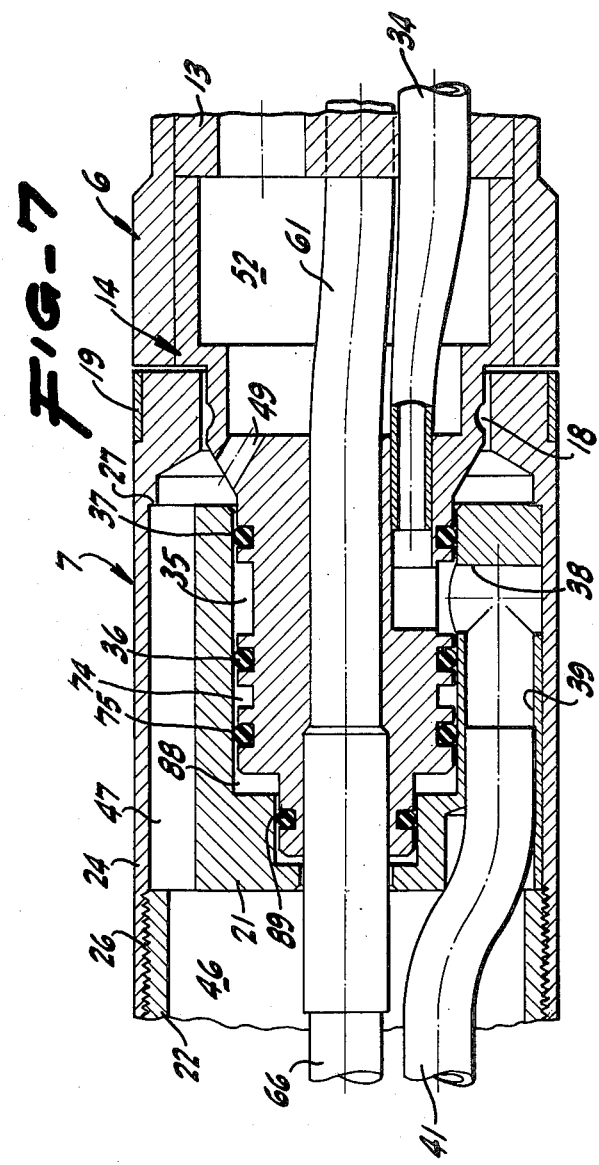
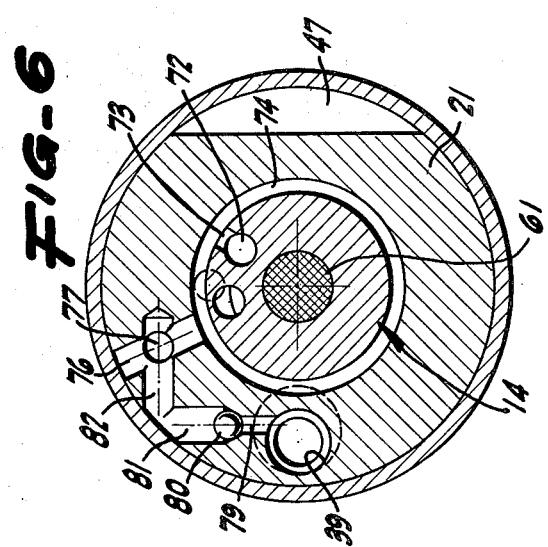

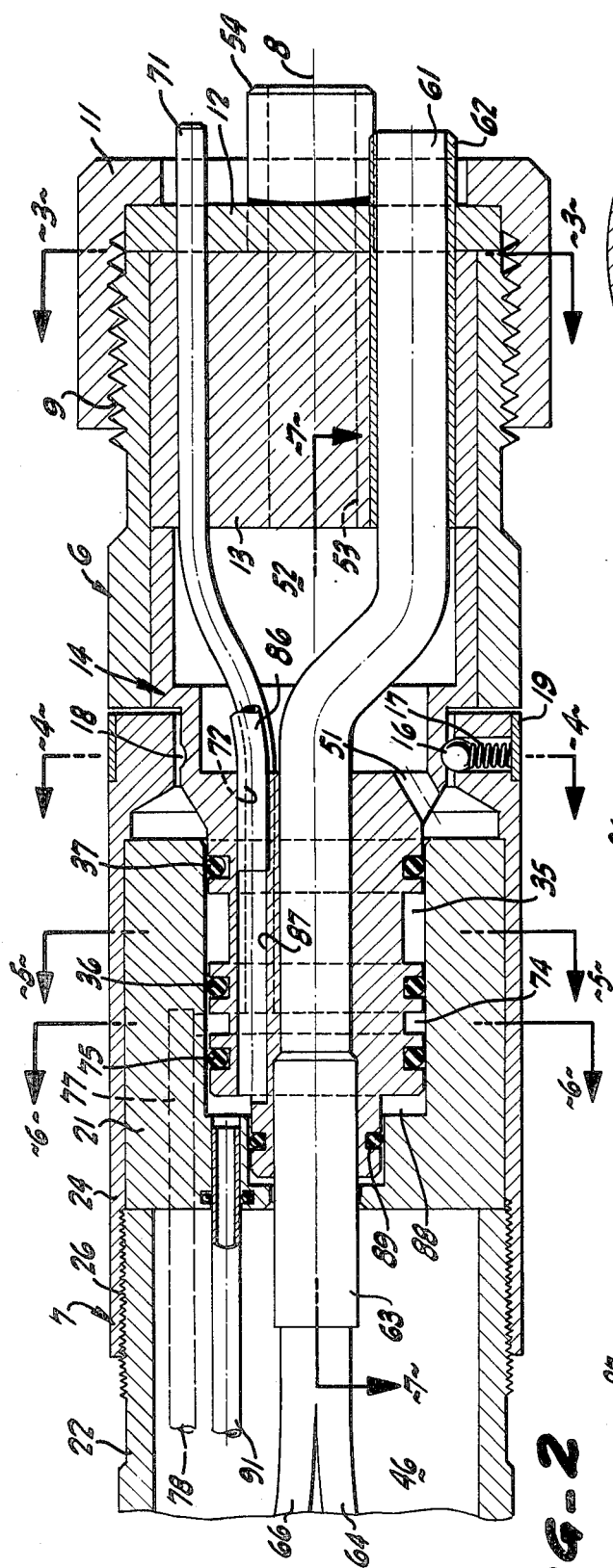
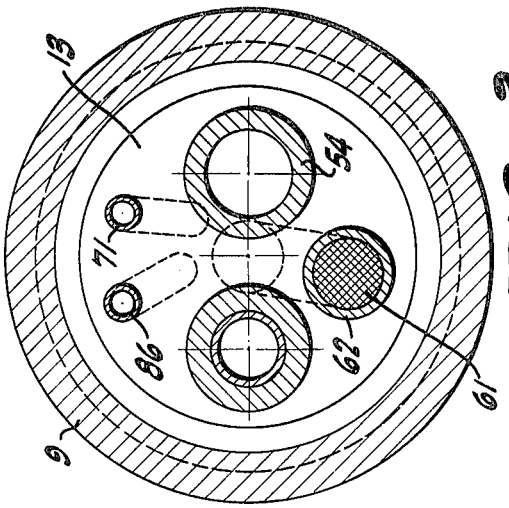
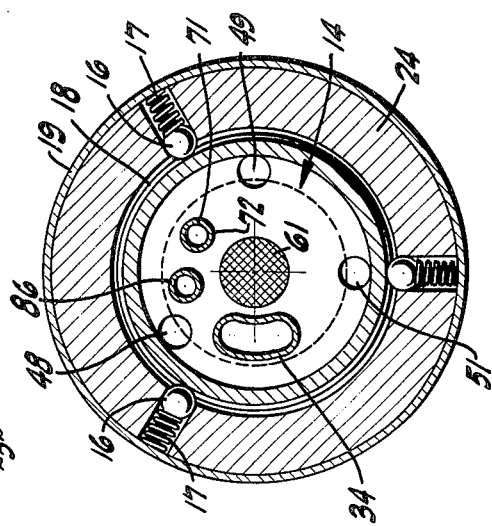
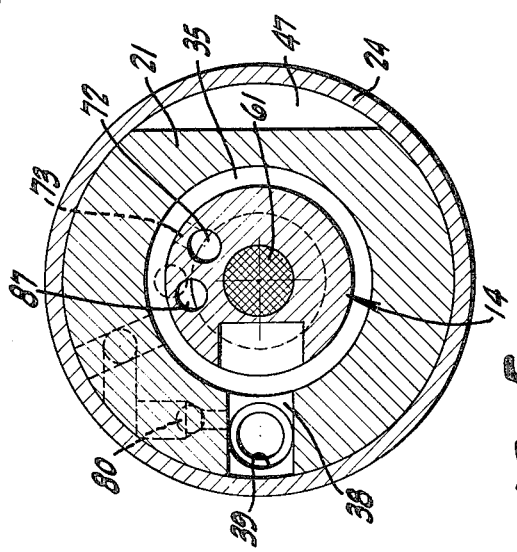

DENTAL HANDPIECE

BRIEF SUMMARY OF THE INVENTION

Our dental handpiece includes a first sleeve and a second sleeve interengaged for relative rotation of the sleeves about a common axis. At one end of one of the sleeves there is a gas turbine carrying a chuck to receive a dental burr. There are devices in both the first and second sleeves for conducting impelling gas to the turbine and for conducting spent or exhaust gas away from the turbine, as well as means for conducting cleaning air to the vicinity of the turbine and for conducting water to the vicinity of the turbine. Also there are optical conductors for carrying light through both sleeves to the area of the turbine. The two sleeves as well as the various conducting means in the sleeves are all arranged to be rotated relative to each other about the common axis. There is thus supplied a dental handpiece having means for impelling a turbine, for supplying water and air to the vicinity of the turbine and for supplying light to the same vicinity. These all swivel with respect to each other, so that the handpiece can be adjusted in a rotatable fashion to suit the user.

BRIEF DESCRIPTION OF THE SEVERAL VIEWS OF THE DRAWINGS

FIG. 1 is a side elevation to an enlarged scale showing the handpiece of the invention.

FIG. 2 is a cross-section, the plane of which is indicated by the line 2—2 of FIG. 1.

FIG. 3 is a cross-section, the plane of which is indicated by the line 3—3 of FIG. 2.

FIG. 4 is a cross-section, the plane of which is indicated by the line 4—4 of FIG. 2.

FIG. 5 is a cross-section, the plane of which is indicated by the line 5—5 of FIG. 2.

FIG. 6 is a cross-section, the plane of which is indicated by the line 6—6 of FIG. 2.

FIG. 7 is a cross-section, the plane of which is indicated by the line 7—7 of FIG. 2.

DETAILED DESCRIPTION

The dental handpiece is inclusive of a first sleeve 6 and a second sleeve 7 connected so as to be relatively rotatable with respect to each other about a common or central, longitudinal axis 8. The first sleeve has a threaded end 9 receiving a finishing ring 11 that is removable and when in place retains a gasket 12 and a guiding block 13. The first sleeve 6 also carries an interior body 14 abutting the guiding block and projecting into the second sleeve 7. The sleeves are axially held together resiliently and in a relatively rotatable fashion by a plurality of circumferentially separated balls 16 having springs 17 pressing them into a groove 18 formed in the body 14. A circumferential band 19 serves as a support and backing for the springs 17.

Within the second sleeve 7 there is an annulus 21 at one end abutting a tube 22 which extends to a turbine housing 23 at one end of the tube 22, abutting the body 21 and forming part of the second sleeve 7. The annulus 21 is held in position by a surrounding part 24 of the second sleeve 7 having threads 26 to interengage the members. There is an abutment shoulder 27 on the part 24 to prevent axial movement of the annulus 21 and the part 24 when they are held together.

Within the housing 23 there is the customary rotary turbine 31 which drives a dental burr chuck 32 having a burr 33 therein, the turbine being appropriately driven by any suitable gas, such as compressed air.

To supply the turbine, there is provided an external source of compressed air or other appropriate gas. This is led into the handpiece through a duct 34 (FIG. 7) which is altered in cross-section to extend into the body 14. Therein the duct 34 takes a right-angle turn toward the outside to feed into a groove 35 in the body 14 and axially isolated by a pair of adjacent O-rings 36 and 37. The groove 35 communicates with a port 38 at the end of a bore 39 in the annulus 21 that surrounds the body 14. The elbow opens into a tube 41 that extends generally axially through the second sleeve and goes to the turbine housing 23 as a supplier of appropriate driving gas to the turbine 31.

Spent or exhaust gas from the turbine is released into the interior space 46 of the tube 22. From there (FIG. 7), it flows into a side channel 47 in the annulus 21 and into an end chamber from which flow proceeds through several inclined bores 48, 49 and 51 into a chamber 52. The flow continues through a bore 53 and extension 54 to the outside with or without an extension hose (not shown).

It is helpful to have excellent illumination of the burr area of the operating field. For that reason, light from a suitable source is led into the handpiece by a light conductor 61, often of many glass or plastic fibers or a single large plastic or glass fiber. These may be suitably clad, if desired. Entrance is through a sleeve 62 going through the gasket 12 and the guiding block 13. The light conductor 61 also goes coaxially through the interior body 14 into a junction tube 63. While a single, separately rotatable conductor can emerge from the tube 63, preferably there are two light leads 64 and 66 emerging on the axis and diverging bilaterally adjacent the burr 33 to supply clear illumination.

Under control by the handpiece user is a supply of compressed air for use in blowing away debris in the operating field. From a suitable source, such air is carried by a tube 71 through the gasket 12 and the guiding block 13 and then into a bore 72 going nearly through the interior body 14. The bore has a radial connector 73 to a circumferential groove 74 (FIG. 2) isolated by a pair of O-rings 36 and 75. As shown especially in FIG. 6, the groove 74 opens into a radial duct 76 communicating with an axial air carrier 77 in the annulus 21 and discharging through a tube 78 ending in the vicinity of the burr 33. This arrangement provides a means, despite the swivelling of the handpiece, by which the operator, by proper valving, can supply from time to time a jet of relatively higher pressure air to the burr region.

There can also be a substantially continuous supply of relatively lower pressure turbine-propelling gas or air to the same burr region. As particularly indicated in FIGS. 6 and 7, the bore 39, supplied through the duct 34, opens into a passage 79. A check valve 80 allows one-way flow into a bore 81 connected by a cross bore 82 to the air carrier 77. Thus, turbine air or gas can flow continuously, past the valve 80 to the burr vicinity, but sporadically valved, higher pressure air from the groove 74 and the carrier 77 cannot flow into and disturb the turbine. The air or gas supply is unaffected by the swivelling motion.

Somewhat similarly, there is afforded a water supply to the burr vicinity. From a valved source (not shown) water is carried by a pipe 86 and bore 87 through the interior body 14 to an end space 88, sealed by an O-ring 89 and the O-ring 75. A water duct 91 continues through the second sleeve tube 22 to a discharge nozzle 92 (FIG. 1) adjacent the burr. Thus, despite the swivel motion provided, there is a continuous path for water.

With the described arrangement, there is provided a dental handpiece of substantially the normal size and "feel" and in which the supply end and the burr end are rotatable or can swivel with respect to each other around a central, longitudinal axis. There is a supply of driving gas or air for the turbine to rotate the burr. There is a supply of light directed at the burr area. There are supplies of controlled cleansing air and cleansing water. All together, these several supplies in a swivelling handpiece provide an advantageous operating instrument for improved dental work.

We claim:

1. A dental handpiece comprising a first sleeve and a second sleeve interengaged for rotation of said sleeves relative to each other about a common axis, a gas turbine having a chuck for a dental burr and mounted at the end of said second sleeve, means in said first sleeve and in said second sleeve and including a swivel connection about said axis for conducting impelling gas to said turbine, means including a first fiber glass light conductor having one portion disposed in said first sleeve and extending therein along said axis and having another portion disposed in said first sleeve and extending off of said axis and thereby fixing said first fiber glass light conductor against rotation relative to said first sleeve, means including a second fiber glass light conductor in said second sleeve having one portion on and extending along said axis in alignment with and facing said one portion of said first fiber glass light conductor and having a plurality of other portions fixed in said second sleeve off of said axis and thereby fixing said second fiber glass light conductor against rotation relative to said second sleeve, a junction tube carried by one of said sleeves and coaxial therewith to receive fiber glass light leads therewithin and configured to accommodate relative rotation between one of said sleeves and one of said light leads, and means for holding said first sleeve and said second sleeve yieldably in axial engagement with each other and with said axial portions of said first and said second fiber glass light conductors in axial continuance of each other.

2. A dental handpiece comprising a first sleeve substantially symmetrical about an axis, a second sleeve substantially symmetrical about said axis and in part surrounding a part of said first sleeve, means on said second sleeve for receiving a burr, means for interconnecting said surrounding part of said second sleeve and said first sleeve for relative rotation of said sleeves about said axis and against ready separation by translation along said axis, a junction tube disposed in one end of said first sleeve and projecting along said axis into said second sleeve, a fiber glass light conductor in part disposed in and extending eccentrically of said first sleeve and in part extending coaxially into said junction tube and rotatable relative thereto with said second sleeve, and fiber glass light leads in part emerging from said junction tube along said axis and in part diverging from each other and from said axis and extending within said second sleeve and emerging near said burr receiving means.

* * * * *